US012636392B2

(12) United States Patent
Kapila et al.

(10) Patent No.: US 12,636,392 B2
(45) Date of Patent: May 26, 2026

(54) DEVICES, METHODS, AND SYSTEMS OF A SELF-SANITIZING LAPTOP

(71) Applicant: Intel Corporation, Santa Clara, CA (US)

(72) Inventors: Smit Kapila, Bangalore (IN); Sean J. W. Lawrence, Bangalore (IN); Min Suet Lim, Gelugor (MY); Akhilesh Rallabandi, Chandler, AZ (US); Prakash Kurma Raju, Bangalore (IN); Joy Poddar, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 432 days.

(21) Appl. No.: 18/324,197

(22) Filed: May 26, 2023

(65) Prior Publication Data

US 2024/0390541 A1     Nov. 28, 2024

(51) Int. Cl.
| | |
|---|---|
| *G01N 23/00* | (2006.01) |
| *A61L 2/10* | (2006.01) |
| *A61L 2/24* | (2006.01) |
| *A61N 5/00* | (2006.01) |
| *G01N 21/00* | (2006.01) |
| *G06F 1/16* | (2006.01) |

(52) U.S. Cl.
CPC ..................................... *A61L 2/24* (2013.01); *A61L 2/10* (2013.01); *G06F 1/1677* (2013.01)

(58) Field of Classification Search
CPC ..... A61L 2/08; A61L 2/24; A61L 2/26; A61L 2/10; G09F 9/33; G09F 1/133617; G02F 1/13338; H05K 7/20145

USPC ............... 422/24; 250/455.11, 454.11, 492.1
See application file for complete search history.

(56) References Cited

U.S. PATENT DOCUMENTS 9,492,576 B1 * 11/2016 Cudak ...................... A61L 2/10

FOREIGN PATENT DOCUMENTS

CN        111900153 A     11/2020

OTHER PUBLICATIONS

Partial European Search Report issued for the corresponding EP patent application No. EP 23207656.2, dated Apr. 9, 2024, 17 pages (For informational purposes only).
Hewlett-Packard Company et al., "Self sanitizing laptop computer using UV-C", research disclosure, Kenneth Mason Publications, 2009, p. 831.

(Continued)

*Primary Examiner* — Monzer R Chorbaji
(74) *Attorney, Agent, or Firm* — Viering, Jentschura & Partner mbB

(57)        ABSTRACT

Disclosed herein are devices, systems, and methods for self-sanitizing a device using the built-in screen display of the device (e.g., a laptop). The device includes a processor configured to execute instructions to determine a relationship between a location of a display of the device and a location of a keyboard surface of the device. The processor is also configured to execute instructions configured to, based on the relationship, enable a sanitization mode on the device and to configure the display to emit light toward the keyboard surface to sanitize the keyboard surface when the sanitization mode is enabled.

20 Claims, 5 Drawing Sheets

(56)                    References Cited

OTHER PUBLICATIONS

Dai, Tianhong et al.; "Blue light for infectious diseases: Propionibacterium acnes, Helicobacter pylori, and beyond?"; published online on Jul. 28, 2012 at https://www.ncbi.nlm.nih.gov/pmc/articles/PMC3438385/; PubMed Central; retrieved on May 22, 2023; 34 pages; National Library of Medicine.

Dai, Tianhong et al.; "Visible Blue Light is Capable of Inactivating Candida albicans and Other Fungal Species"; published on Jul. 1, 2017 at https://www.ncbi.nlm.nih.gov/pmc/articles/PMC5512304/; PubMed Central; retrieved on May 22, 2023; 3 pages; National Library of Medicine.

Quinn, John; "This Is the Most Germ-Infested Item in Your Home, Study Finds"; https://bestlifeonline.com/laptop-germs/; Best Life; retrieved on May 22, 2023; 15 pages.

Espino, Luis; "Does all UV light kill viruses and bacteria?"; https://insights.regencylighting.com/does-all-uv-light-kill-viruses; Regency Lighting; retrieved on May 22, 2023; 14 pages.

Maclean, Michelle et al.; "Inactivation of Bacterial Pathogens following Exposure to Light from a 405-Nanometer Light-Emitting Diode Array"; published on Feb. 6, 2009 at https://www.ncbi.nlm.nih.gov/pmc/articles/PMC2663198/; PubMed Central; retrieved on May 22, 2023; 13 pages; National Library of Medicine.

Vioguard; "Defender™"; https://www.vioguard.com/product/vioguard-defender/; retrieved on May 22, 2023; 6 pages.

Ubuy; "Doctor's Choice UV Sanitizer Box. Personal UV Sterilizer Box. Large UV Light Sanitizer Box fits Masks, Phones, Sleep Aid, Glasses, Bottles, Toothbrush, Pacifier"; https://www.ubuy.co.in/product/1NEJ5KLG-doctor-s-choice-uv-light-sanitizer-personal-uv-sanitizer-large-uv-phone-sanitizer-fits-masks-phones-; retrieved on May 22, 2023; 6 pages.

Amazon; "Amtidy U99 UV Sanitizer, Portable UV Sterilizer Box 99.9% Sterilization for Mask, Cell Phone/Smartphone, Makeup Tools, Keys, Glasses, Multi-Function Mobile Phone Toothbrush Cleaning Box "; https://www.amazon.in/Amtidy-U99-Sterilizer-Sterilization-Multi-Function/dp/B08RYCDPZZ; retrieved on May 22, 2023; 9 pages.

* cited by examiner

UV light

121

110

120

130

110

120

130

101

110

130

Determining a relationship between a location of a display of a device and a
location of a keyboard surface of the device                    410

Enabling a sanitization mode on the device based on the relationship          420

Emitting emit light toward the keyboard surface to sanitize the keyboard
surface when the sanitization mode is enabled                    430

400

500

Enabling, based on a predefined trigger, a sanitization mode on a device, wherein the device includes an upper cover that includes a display screen, wherein the upper cover is connected by a hinge to a lower cover that includes a keyboard

510

Emitting light with a predefined light intensity from the display screen toward the keyboard to sanitize the keyboard

520

DEVICES, METHODS, AND SYSTEMS OF A SELF-SANITIZING LAPTOP

TECHNICAL FIELD

The disclosure relates generally to light-based sanitizing systems, and in particular, to light-based sanitizing systems for sanitizing the keyboard/touchpad area of a laptop.

BACKGROUND

The keyboard/touchpad (also called the "C-cover") of a laptop is likely one of the most germ-infested locations of the laptop, if not one of the most germ-infested locations in one's office/home, perhaps carrying thousands of times more bacteria than even a toilet seat. As work, school, socializing, and entertainment increasingly move on-line, individuals may be using their laptops more than ever before. At the same time, the use of ultraviolet (UV) light to sanitize a surface has become more prevalent, especially as recent attention has been placed on easily-transmissible viruses such as recent coronaviruses. UV light has the ability to kill germs/pathogens like viruses, funguses, and bacteria. For example, UV light in the 200-300 nanometer (nm) wavelength range (e.g., UV-C) is often used to sanitize medical grade equipment, though other wavelengths of light, including visible "blue light" in the 400-490 nm range may also be effective in killing common bacteria, viruses, funguses, and other germs/pathogens.

BRIEF DESCRIPTION OF THE DRAWINGS

In the drawings, like reference characters generally refer to the same parts throughout the different views. The drawings are not necessarily to scale, emphasis instead generally being placed upon illustrating the exemplary principles of the disclosure. In the following description, various exemplary aspects of the disclosure are described with reference to the following drawings, in which.

DESCRIPTION

Figure 1C:
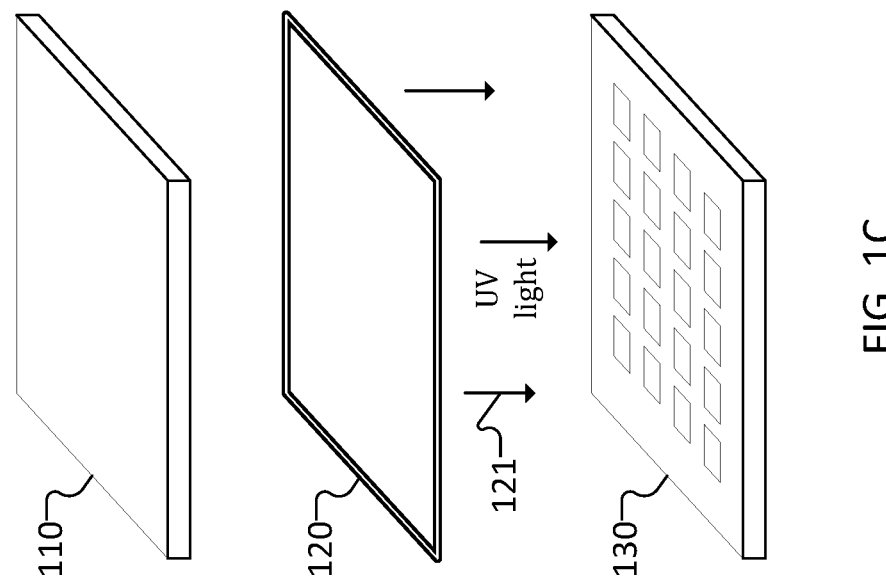
FIG. 1C shows an exploded view of the clamshell laptop of FIG. 1B, where the lid of the clamshell has been closed.

The following detailed description refers to the accompanying drawings that show, by way of illustration, exemplary details and features.

The word "exemplary" is used herein to mean "serving as an example, instance, or illustration." Any aspect or design described herein as "exemplary" is not necessarily to be construed as preferred or advantageous over other aspects or designs.

Throughout the drawings, it should be noted that like reference numbers are used to depict the same or similar elements, features, and structures, unless otherwise noted.

The phrase "at least one" and "one or more" may be understood to include a numerical quantity greater than or equal to one (e.g., one, two, three, four, [ . . . ], etc.). The phrase "at least one of" with regard to a group of elements may be used herein to mean at least one element from the group consisting of the elements. For example, the phrase "at least one of" with regard to a group of elements may be used herein to mean a selection of: one of the listed elements, a plurality of one of the listed elements, a plurality of individual listed elements, or a plurality of a multiple of individual listed elements.

The words "plural" and "multiple" in the description and in the claims expressly refer to a quantity greater than one. Accordingly, any phrases explicitly invoking the aforementioned words (e.g., "plural [elements]", "multiple [elements]") referring to a quantity of elements expressly refers to more than one of the said elements. For instance, the phrase "a plurality" may be understood to include a numerical quantity greater than or equal to two (e.g., two, three, four, five, [ . . . ], etc.).

The phrases "group (of)", "set (of)", "collection (of)", "series (of)", "sequence (of)", "grouping (of)", etc., in the description and in the claims, if any, refer to a quantity equal to or greater than one, i.e., one or more. The terms "proper subset", "reduced subset", and "lesser subset" refer to a subset of a set that is not equal to the set, illustratively, referring to a subset of a set that contains less elements than the set.

The term "data" as used herein may be understood to include information in any suitable analog or digital form, e.g., provided as a file, a portion of a file, a set of files, a signal or stream, a portion of a signal or stream, a set of signals or streams, and the like. Further, the term "data" may also be used to mean a reference to information, e.g., in the form of a pointer. The term "data", however, is not limited to the aforementioned examples and may take various forms and represent any information as understood in the art.

The terms "processor" or "controller" as, for example, used herein may be understood as any kind of technological entity (e.g., hardware, software, and/or a combination of both) that allows handling of data. The data may be handled according to one or more specific functions executed by the processor or controller. Further, a processor or controller as used herein may be understood as any kind of circuit, e.g., any kind of analog or digital circuit. A processor or a controller may thus be or include an analog circuit, digital circuit, mixed-signal circuit, software, firmware, logic circuit, processor, microprocessor, Central Processing Unit (CPU), Graphics Processing Unit (GPU), Digital Signal Processor (DSP), Field Programmable Gate Array (FPGA), integrated circuit, Application Specific Integrated Circuit (ASIC), etc., or any combination thereof. Any other kind of implementation of the respective functions, which will be described below in further detail, may also be understood as a processor, controller, or logic circuit. It is understood that any two (or more) of the processors, controllers, or logic circuits detailed herein may be realized as a single entity with equivalent functionality or the like, and conversely that any single processor, controller, or logic circuit detailed herein may be realized as two (or more) separate entities with equivalent functionality or the like.

As used herein, "memory" is understood as a computer-readable medium (e.g., a non-transitory computer-readable medium) in which data or information can be stored for retrieval. References to "memory" included herein may thus be understood as referring to volatile or non-volatile memory, including random access memory (RAM), read-only memory (ROM), flash memory, solid-state storage, magnetic tape, hard disk drive, optical drive, 3D XPoint™, among others, or any combination thereof. Registers, shift registers, processor registers, data buffers, among others, are also embraced herein by the term memory. The term "software" refers to any type of executable instruction, including firmware.

Unless explicitly specified, the term "transmit" encompasses both direct (point-to-point) and indirect transmission (via one or more intermediary points). Similarly, the term "receive" encompasses both direct and indirect reception. Furthermore, the terms "transmit," "receive," "communicate," and other similar terms encompass both physical transmission (e.g., the transmission of radio signals) and logical transmission (e.g., the transmission of digital data over a logical software-level connection). For example, a processor or controller may transmit or receive data over a software-level connection with another processor or controller in the form of radio signals, where the physical transmission and reception is handled by radio-layer components such as radio frequency (RF) transceivers and antennas, and the logical transmission and reception over the software-level connection is performed by the processors or controllers. The term "communicate" encompasses one or both of transmitting and receiving, i.e., unidirectional or bidirectional communication in one or both of the incoming and outgoing directions. The term "calculate" encompasses both "direct" calculations via a mathematical expression/formula/relationship and 'indirect' calculations via lookup or hash tables and other array indexing or searching operations.

Reference is made throughout the specification to a "laptop," which should be understood as merely one example of the form factor of the device to which the self-sanitizing system disclosed may apply. Thus, references to a laptop should be understood as being equally applicable to and disclosed for use in any type of device, including, as additional non-limiting examples, a phone, a smartphone, a tablet, a smartwatch, a wearable, a desktop computer, etc. that may have or be configured to use a display (e.g., a monitor, a screen, a projector, etc.) and input device (e.g., keyboard, touchpad, touchscreen, button(s), etc.).

As noted above, laptops are often germ-infested locations, and in particular, the keyboard/touchpad area ("C-cover"). While it is possible to clean the laptop's keyboard area by washing it (e.g., with soap/water) or using a sanitizing spray, such methods may damage the keyboard/touchpad due to scrubbing of the surface and/or due to contact to abrasive chemicals and/or liquids that may harmfully penetrate the keyboard/touchpad surface. Such surface cleaning is generally a manual, irregular process, and the spaces between keys and at interfaces of the keyboard may be difficult to clean effectively, not to mention that many pathogens and microbes may be resistant to common cleaning sprays/disinfectants. In addition, while ultraviolet (UV) light is known to be able to kill germs/pathogens like viruses, funguses, and bacteria, conventional UV-light-based sanitizing systems are often separate units, where the laptop must be inserted into a specially-designed UV-light container (such as a drawer, box, cabinet, etc.) to radiate the laptop with UV light. Such UV-light containers, however, may be disadvantageous because they require purchase of a separate device and may serve to disinfect only the exposed surfaces (e.g., the outer surface) of the laptop, which may not include the keyboard area.

Unlike such conventional UV-light containers, the self-sanitizing system disclosed below may sanitize the keyboard area of a device automatically, without the need for a separate sanitizing unit. Laptops typically have a display screen that folds over the keyboard area (e.g., in what is called a "clamshell" type design), and the self-sanitizing system may enable a sanitizing mode that configures light that is within the available spectrum of light emitted from a typical computer display (such as visible light in the "blue light" range of 400-490 nm) to be emitted from the display screen (e.g., the built-in liquid-crystal display (LCD)/light-emitting-diode (LED) display of the device/laptop) towards the keyboard area to sanitize the keyboard/touch-pad. By configuring the display to emit such light for a given amount of time, the emitted light may sanitize the keyboard/touch pad. Advantageously, the sanitization mode may be enabled on a scheduled/regular basis (and when the device/laptop is not otherwise in use) so as to regularly, efficiently, and effectively sanitize the keyboard area, reducing the level of germs/pathogens like viruses, funguses, and bacteria, carried by the device/laptop.

In the keyboard sanitization mode, the self-sanitizing system may configure the screen to emit light for a pre-defined period of time with a predefined light setting that may sanitize the keyboard. For example, the self-sanitizing system may configure the device's display to emit certain light in the available spectrum of light from the display. For example, the self-sanitizing system may configure the display to emit 200-300 nm UV light (e.g., UV-C, if such light is available from the display or from additional, special UV emitters that have been added to the laptop/display), visible light in the 400-490 nm range (e.g., "blue light"), or any other wavelength of light that may be available from the display and effective for killing germs/pathogens like bacteria, viruses, funguses, and other microbes. When the device lid is closed (e.g., in a clamshell form factor that is common to laptops, where the screen faces the keyboard when the lid is closed), the self-sanitizing system may activate the display to emit light directly onto the keyboard/touchpad and in a very close proximity. In a typical laptop, for example, there may be less than a 1 mm gap between the display screen (e.g., its location) and the keyboard (e.g., its location) of a clamshell form factor. In addition, the self-sanitizing system may configure the light emitted from the device's display to have a particular combination of light wavelengths and associated power levels so as to enhance, maximize, increase, etc. the sanitizing ability. For example, the self-sanitizing system may configure the device's display to emit "blue light" (e.g., visible light in the 400-490 nm range) at a high intensity while minimizing other wavelengths of light (e.g., red and green light), as blue light may be an effective sanitizing treatment against harmful germs/pathogens such as bacteria, viruses, funguses-even for those species that may be resistant to other types of manual treatments, such as a disinfecting spray.

The keyboard sanitization mode may be cost effective to implement on an existing laptop because there are little to no new components that need to be added to the typical laptop (e.g., no additional bill of materials ("BOM") costs) and little to no impact on the formfactor of the laptop clamshell (e.g., no impact to the thickness of the laptop, system hardware, sensors, inputs/outputs, chassis ID/UX, lid open/close detection, etc.). The self-sanitizing system may utilize existing hardware, software, and/or embedded controller (EC) solutions for implementing the keyboard sanitization mode.

In addition, the keyboard sanitization mode may have a particularly low-impact with respect to the baseline performance of a device/laptop, where the self-sanitizing system may activate or deactivate the keyboard sanitization mode according to the preferences of the system/user. For example, the self-sanitizing system may disable the sanitization cycle when the computer is not connected to an external power source and/or when battery power is below a given threshold. The self-sanitizing system may utilize existing performance tuning features (such as Dynamic Tuning Technology (DTT) or iGFX) to control enabling/disabling the keyboard sanitization mode.

In addition, the keyboard sanitization mode may also be a particularly safe way of sanitizing the keyboard area of a laptop because the self-sanitizing system may activate the sanitization mode after the laptop lid is closed. In this manner, the user will not be exposed to the configured light used to sanitize the laptop. As should be appreciated, while typical laptop screens output only safe wavelengths of visible light, the device may have (or be designed to have) a display (or another source of emitted light) that is capable of outputting other wavelengths of UV light (e.g., 200-300 nm UV light), including those wavelengths that may be harmful to humans if directly exposed.

Figure 1A:
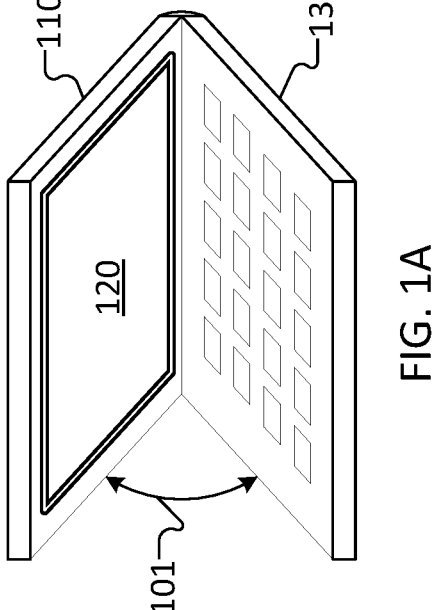
FIG. 1A shows an exemplary self-sanitizing system in the form of a clamshell laptop, where the lid of the clamshell is open.
Figure 1B:
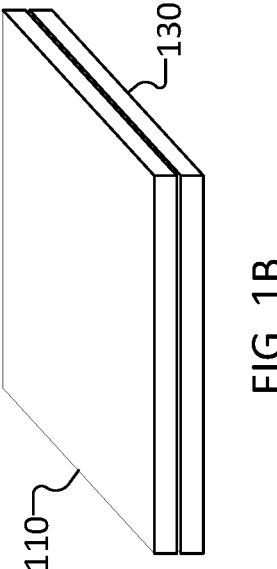
FIG. 1B shows the clamshell laptop of FIG. 1A, where the lid of the clamshell has been closed.

Referring to FIGS. 1A, 1B, and 1C, these figures show an exemplary self-sanitizing system in the form of a clamshell laptop. FIG. 1A shows the clamshell laptop in the open position as it is being closed, FIG. 1B shows the clamshell laptop in the closed position after it has been closed, and FIG. 1C shows an exploded view of FIG. 1B so that the parts of the clamshell laptop can be better seen. In particular, the clamshell laptop in FIGS. 1A, 1B, and 1C includes a top cover 110 (also referred to as an "A-cover") that includes a display screen 120 (also referred to as a "B-cover"), and a keyboard 130 (also referred to as a "C-cover"). In this clamshell design, the angle 101 between the top cover 110 and the keyboard 130 may be adjusted so that the laptop is in various positions. As should be understood, angle 101 may vary from 0 degrees (closed) to nearly 360 degrees (open, in a so-called tablet mode), depending on the type of mechanical and electrical connections between the top cover 110 and the keyboard 130. Angle 101 may be varied so that the laptop is in an "open" position, where the display screen 120 is visible to the user and the keyboard 130 is accessible to the user, an example of which is shown in FIG. 1A. Angle 101 may also be varied so that the laptop is in a "closed" position, where there the surface defined by the top cover 110 is flush with the surface defined by the keyboard 130 (e.g., angle 101 is zero), as shown in FIG. 1B.

In FIG. 1B, because the top cover 110 is flush with the keyboard 130, display screen 120 is not visible in FIG. 1B. Thus, an exploded view is provided in FIG. 1C, which shows how the top cover 110, display screen 120, and keyboard 130 stack up when in the closed position of FIG. 1B, where the display screen 120 faces the keyboard 130. The self-sanitizing system may activate the keyboard sanitization mode when the laptop is in the closed position, when, as shown in FIG. 1C, may configure the display screen 120 to emit a configuration of light 121 towards the keyboard 130. As discussed above, the self-sanitizing system may configure the display screen 120 so that the configuration of light 121 is a "blue light" or other selected wavelengths of light that are effective at sanitizing surfaces. The self-sanitizing system may configure the display screen 120 so that the "blue light" (or other selected wavelength(s) of light) is brighter than other wavelengths of light (e.g., the blue light has a higher luminosity than other wavelengths of light).

Figure 2:
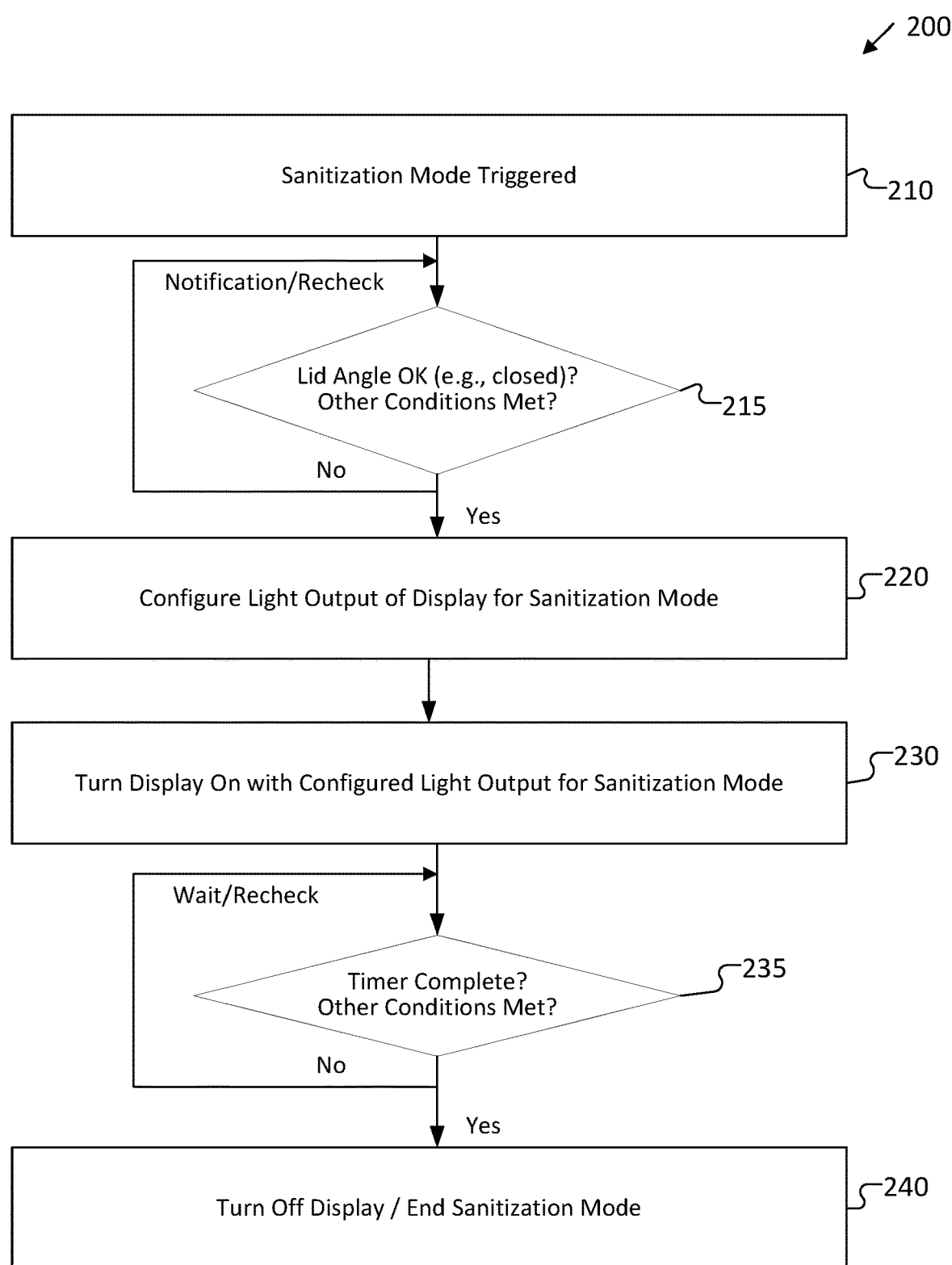
FIG. 2 illustrates an example process that a self-sanitizing device may use to sanitize its keyboard using its built-in display.

FIG. 2 shows a process 200 that a self-sanitizing system may use to sanitize the keyboard area of a device (e.g., a laptop) using its built-in display. In 210, for example, the self-sanitizing system may detect a trigger to enter sanitization mode. The trigger may be any type of trigger that indicates sanitization mode should begin, including, for example, the passage of certain amount of time since the last sanitization, a change in position of the device or the angle of the device's top cover (e.g., its display) with respect to its keyboard, a user request to activate sanitization mode, etc.

Next, the self-sanitizing system may check, in 215, the angle of the top cover with respect to the keyboard to ensure that the lid is closed and/or that the display screen is facing the keyboard area. For example, the self-sanitizing system may check the angle of the top cover to determine whether it satisfies a predefined criterion (e.g., whether the device is in a closed position (e.g., top cover/display is flush with the keyboard), the angle is below a threshold minimum angle at which the light emitted by the display is directed towards the keyboard area, etc.). The self-sanitizing system may also check whether other criteria are met. Examples of other criteria may include whether the device's battery has a sufficient level of charge, whether the device is connected to an external power source, whether the device is scheduled to run other processes, etc. If the conditions are not met, the self-sanitizing system may generate a message to be sent or displayed to the user (e.g., a notification message), indicating that sanitization mode is supposed to start, that the required preconditions have not been satisfied (e.g., lid not closed, lid not at the correct angle, etc.), and/or what must be done to satisfy the preconditions (e.g., close the lid, tilt its angle toward the keyboard, etc.).

Once the self-sanitizing system determines that the preconditions are met, the self-sanitizing system may, in 220, configure the light output settings of the display for sanitization mode. The light output settings may, for example, include the particular wavelengths of light that should be emitted from the display when it is switched on, the corresponding intensity level(s) of the light, etc. (e.g., setting blue light wavelengths to the highest intensity and switching off red, green, and other wavelengths of light). The self-sanitizing system may then, in 230, instruct the display to switch on (e.g., output light from the display) with the configuration settings for sanitization mode. For example, the self-sanitizing system may utilize the graphics controller/application processor of the device. In the sanitization mode, the graphics controller may be configured to increase the display's blue-light output (or other desired wavelengths of light) that are effective for sanitizing the keyboard surface.

Next, the self-sanitizing system may determine, in 235, whether a threshold amount of time has elapsed or whether other predefined criteria have been met for ending sanitization mode and switching off the display. For example, the self-sanitizing system may instruct the display to end sanitization mode by switching off the display after a threshold amount of time has lapsed (e.g., after 30 seconds, after 5 minutes, after 10 minutes, after 60 minutes, etc.). As another example, the self-sanitizing system may instruct the display to end sanitization mode and switch off the display if the device is unplugged from its external power source, if the device's battery level falls below a predefined threshold level, if the device's lid is opened, if the angle of the device's lid changes, if a human comes within a threshold proximity of the device, etc. Once the threshold amount of time has elapsed and/or other predefined criteria have been met, the self-sanitizing system may, in 240, turn off the display and end sanitization mode.

Figure 3:
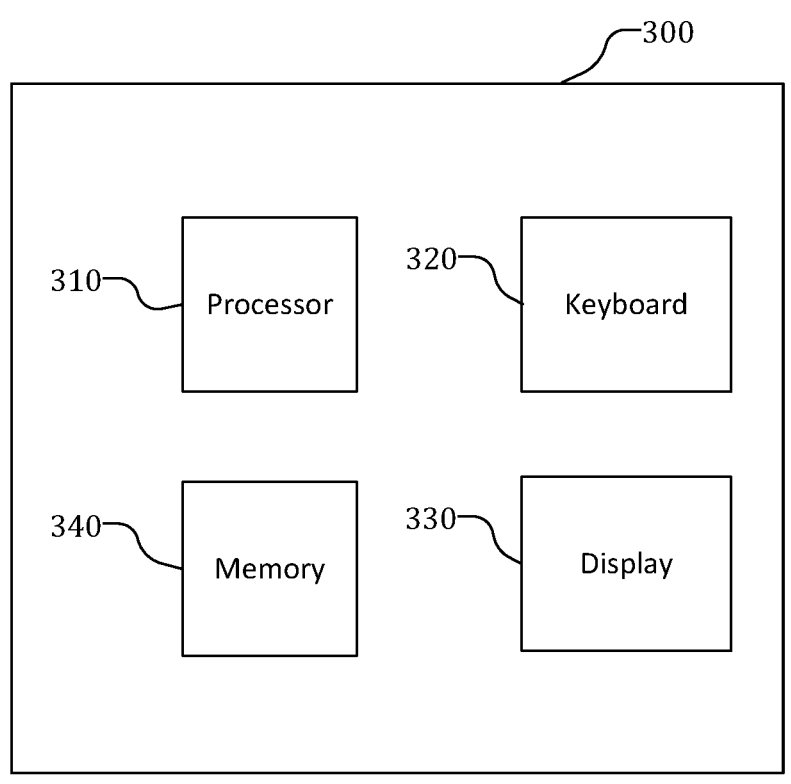
FIG. 3 shows an exemplary schematic drawing of a self-sanitizing device.

FIG. 3 is a schematic drawing illustrating a device 300 that self-sanitizes (e.g., a self-sanitizing laptop). Device 300 may include any of the features of the self-sanitizing systems described above and with respect to FIGS. 1-2. The device 300 of FIG. 3 may be implemented as a device, a method, and/or a computer readable medium that, when executed, performs any of the features of the self-sanitizing systems described above. It should be understood that device 300 is only an example, and other configurations may be possible that include, for example, different components or additional components.

Device 300 (e.g., a laptop) includes a processor 310 configured to execute computer instructions to determine a relationship (e.g. a positional relationship) between a location of a display 330 of device 300 and a location of a keyboard 320 (e.g. the laptop's keyboard, touchpad, trackpad, etc. that may be part of the C-cover and faces the display 330 when closed) of device 300. Processor 310 is also configured to enable a sanitization mode on device 300 based on the relationship and cause, when the sanitization mode is enabled, display 330 to emit light toward the keyboard 320 to sanitize the keyboard 320.

Furthermore, in addition to or in combination with any of the features described in this or the preceding paragraph with respect to device 300, the relationship may include an angle of the display 330 with respect to the keyboard 320. Furthermore, in addition to or in combination with any of the features described in this or the preceding paragraph, the relationship may include a proximity of display 330 to keyboard 320. Furthermore, in addition to or in combination with any of the features described in this or the preceding paragraph, keyboard 320 may include a touchpad. Furthermore, in addition to or in combination with any of the features described in this or the preceding paragraph, device 300 may further include a memory 340 to store the relationship. Furthermore, in addition to or in combination with any of the features described in this or the preceding paragraph, the relationship may include a lid-closed mode, wherein display 330 is flush (e.g., on all sides) with keyboard 320 when in the lid-closed mode.

Furthermore, in addition to or in combination with any of the features described in this or the preceding two paragraphs, device 300 may be a laptop and display 330 may connect to an A-cover of the laptop, wherein display 330 may include a B-cover of the laptop, wherein keyboard 320 may include a C-cover of the laptop. Furthermore, in addition to or in combination with any of the features described in this or the preceding two paragraphs, processor 310 may be configured to execute computer instructions to enable the sanitization mode for a predefined time period and disable the sanitization mode after the predefined time period. Furthermore, in addition to or in combination with any of the features described in this or the preceding two paragraphs, processor 310 may be configured to execute computer instructions to determine the predefined time period based on an intensity level with which display 330 is caused to emit light toward keyboard 320. Furthermore, in addition to or in combination with any of the features described in this or the preceding two paragraphs, the computer instructions may cause display 330, when the sanitization mode is enabled, to adjust a predefined wavelength configuration of the light to sanitize keyboard 320.

Furthermore, in addition to or in combination with any of the features described in this or the preceding three paragraphs with respect to device 300, the predefined wavelength configuration may include a blue wavelength of light with an intensity that is higher than other wavelengths of the light. Furthermore, in addition to or in combination with any of the features described in this or the preceding three paragraphs, the blue wavelength of light may be between about 400 and about 500 nanometers. Furthermore, in addition to or in combination with any of the features described in this or the preceding three paragraphs, processor 310 may be configured to execute computer instructions to enable the sanitization mode based on a power mode of device 300. Furthermore, in addition to or in combination with any of the features described in this or the preceding three paragraphs, the power mode may include a battery-powered mode or an adapter-powered mode. Furthermore, in addition to or in combination with any of the features described in this or the preceding three paragraphs, processor 310 may be configured to execute computer instructions to disable the sanitization mode based on an end-sanitization event.

Furthermore, in addition to or in combination with any of the features described in this or the preceding four paragraphs, processor 310 may be configured to execute computer instructions to enable the sanitization mode based on a trigger event. Furthermore, in addition to or in combination with any of the features described in this or the preceding four paragraphs, the trigger event may include an elapsed time after a previous self-sanitization of device 300. Furthermore, in addition to or in combination with any of the features described in this or the preceding four paragraphs, the trigger event may include a change of a usage activity level of device 300. Furthermore, in addition to or in combination with any of the features described in this or the preceding four paragraphs, the trigger event may include reaching a predefined battery charge level of a battery of device 300. Furthermore, in addition to or in combination with any of the features described in this or the preceding four paragraphs, Furthermore, in addition to or in combination with any of the features described in this or the preceding four paragraphs, the end-sanitization event may include an elapsed time after enabling the sanitization mode. Furthermore, in addition to or in combination with any of the features described in this or the preceding four paragraphs, the end-sanitization event may include a change of a usage activity level of device 300. Furthermore, in addition to or in combination with any of the features described in this or the preceding four paragraphs, the end-sanitization event may include reaching a predefined battery charge level of a battery of device 300. Furthermore, in addition to or in combination with any of the features described in this or the preceding four paragraphs, the end-sanitization event may include a change in the relationship between display 330 and keyboard 320.

Device 300 may be a system (e.g., a self-sanitizing laptop) that includes an upper cover, a lower cover, and a processor 310, where the upper cover includes a display 330 and the lower cover includes a keyboard 320. In addition, the upper cover is connected by a hinge to the lower cover in a clamshell configuration. In addition, processor 310 is configured to execute instructions to enable a sanitization mode in the clamshell configuration based on a predefined trigger to cause the display 330 to emit light with a predefined light intensity toward keyboard 320 to sanitize keyboard 320 when the sanitization mode is enabled.

Furthermore, in addition to or in combination with any of the features described in this or the preceding paragraph, the predefined trigger may include a relationship between the upper cover and the lower cover. Furthermore, in addition to or in combination with any of the features described in this or the preceding paragraph, the clamshell configuration may provide an adjustable angle between the upper cover and the lower cover, wherein the relationship includes whether the adjustable angle satisfies a predefined angular criterion (e.g., whether the adjustable angle is zero (e.g., the lid is closed), is less than 5 degrees (e.g., the lid is mostly closed), is less than 20 degrees (e.g., the lid is partially closed), etc.). Furthermore, in addition to or in combination with any of the features described in this or the preceding paragraph, the relationship may include a lid-closed mode, wherein the upper cover may be flush with the lower cover when in the lid-closed mode. Furthermore, in addition to or in combination with any of the features described in this or the preceding paragraph, the predefined trigger may include whether an amount of time has elapsed (e.g., since a last sanitization of device 300). Furthermore, in addition to or in combination with any of the features described in this or the preceding paragraph, the predefined trigger may include a change of a usage activity level of device 300. Furthermore, in addition to or in combination with any of the features described in this or the preceding four paragraphs, the predefined trigger may include reaching a predefined battery charge level of a battery of device 300.

Furthermore, in addition to or in combination with any of the features described in this or the preceding two paragraphs, keyboard 320 may include an array of keys and/or a touchpad. Furthermore, in addition to or in combination with any of the features described in this or the preceding two paragraphs, device 300 further includes a memory 340 to store the predefined light intensity, the sanitization mode, and/or the predefined trigger. Furthermore, in addition to or in combination with any of the features described in this or the preceding two paragraphs, processor 310 may be configured to execute computer instructions to enable the sanitization mode for a predefined time period and disable the sanitization mode after the predefined time period. Furthermore, in addition to or in combination with any of the features described in this or the preceding two paragraphs, the predefined time period may be based on the predefined light intensity. Furthermore, in addition to or in combination with any of the features described in this or the preceding two paragraphs, the predefined light intensity may include a predefined wavelength configuration of the light emitted by display 330 to sanitize keyboard 320.

Furthermore, in addition to or in combination with any of the features described in this or the preceding three paragraphs with respect to device 300, the predefined wavelength configuration may include blue wavelengths of light with an intensity that is higher than other wavelengths of the light emitted by display 330. Furthermore, in addition to or in combination with any of the features described in this or the preceding three paragraphs, the predefined wavelength configuration may include light wavelengths of about 400 nanometers to about 500 nanometers. Furthermore, in addition to or in combination with any of the features described in this or the preceding three paragraphs, processor 310 may be configured to execute computer instructions to enable the sanitization mode based on a power mode of device 300. Furthermore, in addition to or in combination with any of the features described in this or the preceding three paragraphs, the power mode may include a battery-powered mode or an adapter-powered mode Furthermore, in addition to or in combination with any of the features described in this or the preceding four paragraphs, processor 310 may be configured to execute computer instructions to disable the sanitization mode based on an end-sanitization event. Furthermore, in addition to or in combination with any of the features described in this or the preceding four paragraphs, the end-sanitization event may include an elapsed time after enabling the sanitization mode. Furthermore, in addition to or in combination with any of the features described in this or the preceding four paragraphs, the end-sanitization event may include a change of a usage activity level of device 300. Furthermore, in addition to or in combination with any of the features described in this or the preceding four paragraphs, the end-sanitization event may include reaching a predefined battery charge level of a battery of device 300. Furthermore, in addition to or in combination with any of the features described in this or the preceding four paragraphs, the end-sanitization event may include a change in a relationship between a location of display 330 and a location of keyboard 320.

Figure 4:
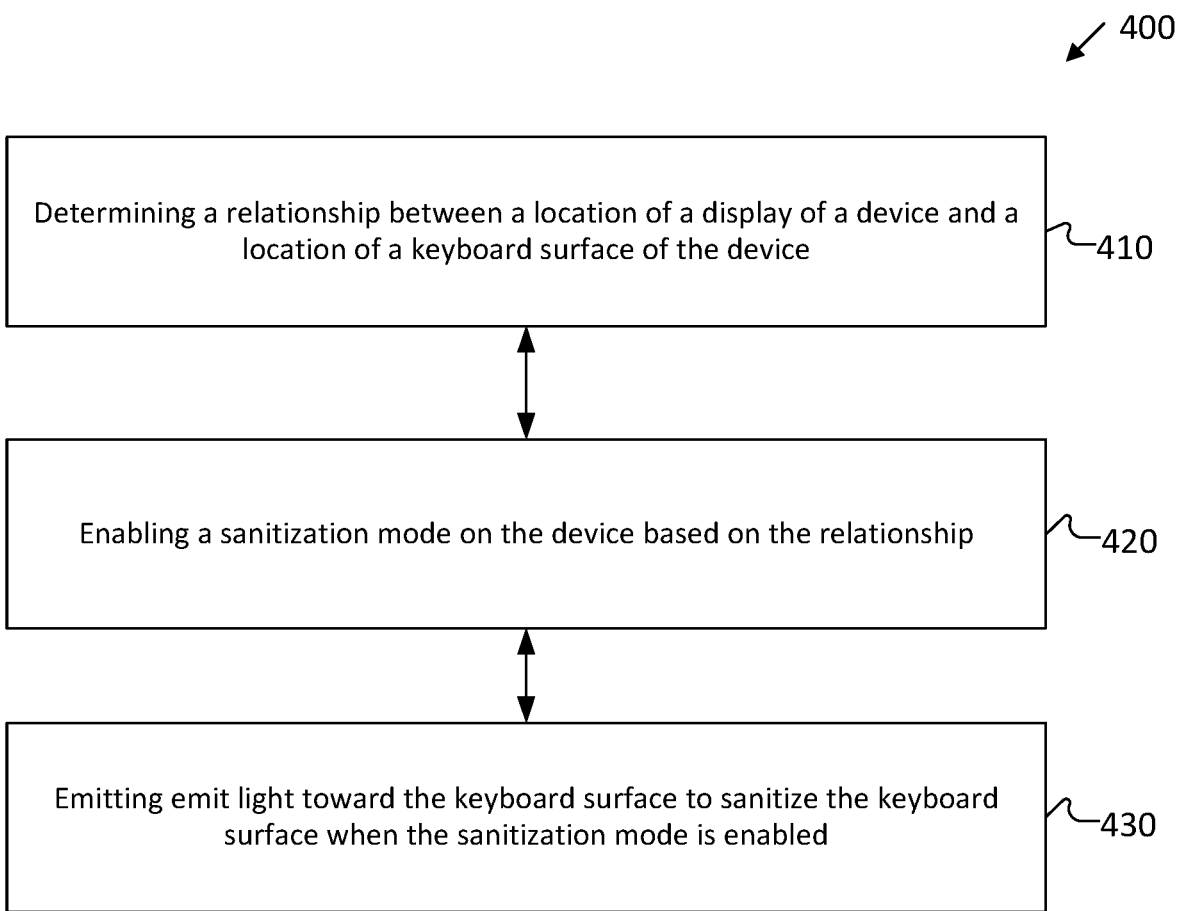
FIG. 4 depicts a schematic flow diagram of an exemplary method for self-sanitizing a device.

FIG. 4 depicts a schematic flow diagram of a method 400 for a self-sanitizing system (e.g., a laptop). Method 400 may implement any of the features of the self-sanitizing systems described above (e.g., the self-sanitizing device of FIG. 1, the process 200 of FIG. 2, and the device 300 of FIG. 3). Method 400 includes, in 410, determining a relationship between a location of a display of the device and a location of a keyboard surface of the device. Method 400 also includes, in 420, enabling a sanitization mode on the device based on the relationship. Method 400 also includes, in 430, emitting light from the display toward the keyboard surface to sanitize the keyboard surface when the sanitization mode is enabled.

Figure 5:
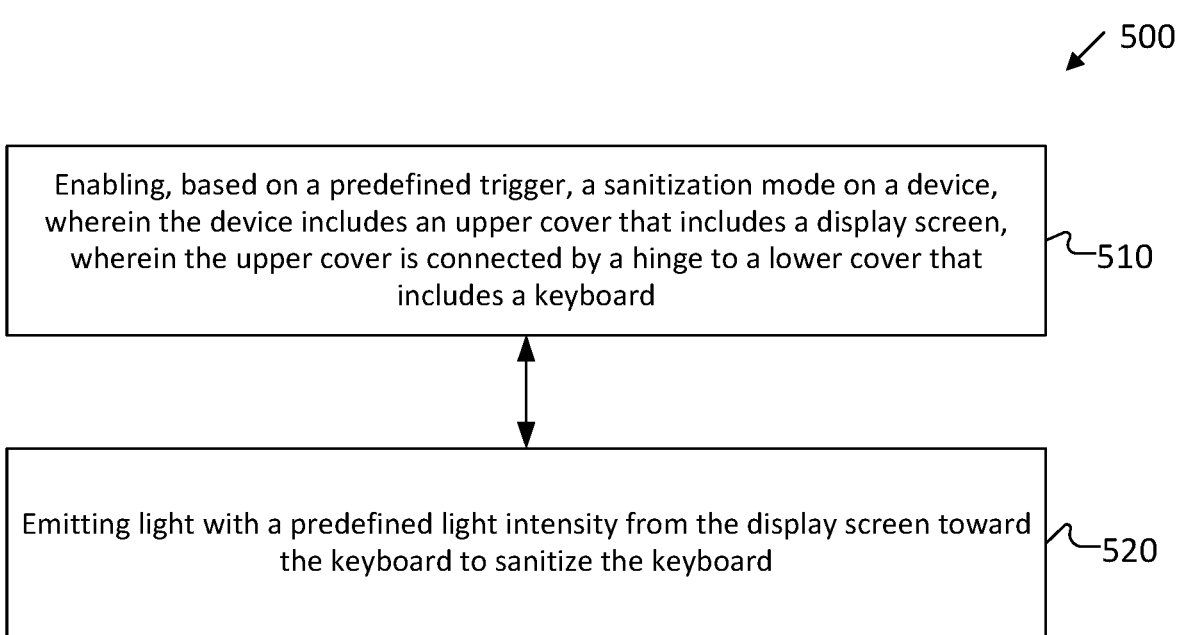
FIG. 5 illustrates a schematic flow diagram of an exemplary method for self-sanitizing a device.

FIG. 5 depicts a schematic flow diagram of a method 500 for self-sanitizing a system (e.g., a laptop). Method 500 may implement any of the features of the self-sanitizing systems described above (e.g., the self-sanitizing device of FIG. 1, the process 200 of FIG. 2, the device 300 of FIG. 3, and the method 500 of FIG. 4). Method 500 is for self-sanitizing a device (e.g., a laptop), wherein the device includes an upper cover including a display screen and a lower cover including a keyboard, wherein the upper cover is connected by a hinge to the lower cover in a clamshell configuration. Method 500 includes, in 510, enabling, based on a predefined trigger, a sanitization mode on the device. Method 500 also includes, in 520, emitting light with a predefined light intensity from the display screen toward the keyboard to sanitize the keyboard.

In the following, various examples are provided that may include one or more features of the self-sanitizing systems described above with respect to FIGS. 1-5. It may be intended that aspects described in relation to the devices may apply also to the described method(s), and vice versa.

Example 1 is a device (e.g., a laptop) (e.g., for self-sanitizing the device), the device including a processor configured to execute computer instructions to determine a relationship between a location of a display of the device and a keyboard surface of the device. The processor is also configured to execute computer instructions to enable a sanitization mode on the device based on the relationship and to cause the display to emit light toward the keyboard surface to sanitize the keyboard surface when the sanitization mode is enabled.

Example 2 is the device of example 1, wherein the relationship includes an angle of the display with respect to the keyboard surface.

Example 3 is the device of either one of examples 1 or 2, wherein the relationship includes a proximity of the display to the keyboard surface.

Example 4 is the device of any one of examples 1 to 3, wherein the keyboard surface includes a keyboard and/or a touchpad.

Example 5 is the device of any one of examples 1 to 4, the device further including a memory to store the relationship.

Example 6 is the device of any one of examples 1 to 5, wherein the relationship includes a lid-closed mode, wherein the display is flush (e.g., on all sides) with the keyboard surface when in the lid-closed mode.

Example 7 is the device of any one of examples 1 to 6, wherein the device comprises a laptop, wherein the display is connected to an A-cover of the laptop, wherein the display includes a B-cover of the laptop, wherein the keyboard surface includes a C-cover of the laptop.

Example 8 is the device of any one of examples 1 to 7, wherein the processor is configured to execute computer instructions to enable the sanitization mode for a predefined time period and disable the sanitization mode after the predefined time period.

Example 9 is the device of example 8, wherein the processor is configured to execute computer instructions to determine the predefined time period based on an intensity level with which the display is caused to emit light toward the keyboard surface.

Example 10 is the device of any one of examples 1 to 9, wherein the computer instructions cause the display, when the sanitization mode is enabled, to adjust a predefined wavelength configuration of the light to sanitize the keyboard surface.

Example 11 is the device of example 10, wherein the predefined wavelength configuration includes a blue wavelength of light with an intensity that is higher than other wavelengths of the light.

Example 12 is the device of example 11, wherein the blue wavelength of light is between about 400 and about 500 nanometers.

Example 13 is the device of any one of examples 1 to 12, wherein the processor is configured to execute computer instructions to enable the sanitization mode based on a power mode of the device.

Example 14 is the device of example 13, wherein the power mode includes a battery-powered mode or an adapter-powered mode.

Example 15 is the device of any one of examples 1 to 14, wherein the processor is configured to execute computer instructions to enable the sanitization mode based on a trigger event.

Example 16 is the device of example 15, wherein the trigger event includes an elapsed time after a previous self-sanitization of the device.

Example 17 is the device of either one of examples 15 or 16, wherein the trigger event includes a change of a usage activity level of the device.

Example 18 is the device of any one of examples 15 to 17, wherein the trigger event includes reaching a predefined battery charge level of a battery of the device.

Example 19 is the device of any one of examples 1 to 18, wherein the processor is configured to execute computer instructions to disable the sanitization mode based on an end-sanitization event.

Example 20 is the device of example 19, wherein the end-sanitization event includes an elapsed time after enabling the sanitization mode.

Example 21 is the device of either one of examples 19 or 20, wherein the end-sanitization event includes a change of a usage activity level of the device.

Example 22 is the device of any one of examples 19 to 21, wherein the end-sanitization event includes reaching a predefined battery charge level of a battery of the device.

Example 23 is the device of any one of examples 19 to 22, wherein the end-sanitization event includes a change in the relationship between a location of the display and a location of the keyboard surface.

Example 24 is a system (e.g., a self-sanitizing laptop) including an upper cover including a display screen, a lower cover including a keyboard, wherein the upper cover is connected to the lower cover in a clamshell configuration by a hinge, and processor. The processor is configured to execute computer instructions to enable a sanitization mode in the clamshell configuration based on a predefined trigger and to cause the display screen to emit light with a predefined light intensity toward the keyboard to sanitize the keyboard when the sanitization mode is enabled.

Example 25 is the system of example 24, wherein the predefined trigger includes a relationship between the upper cover and the lower cover.

Example 26 is the system of example 25, wherein the clamshell configuration provides an adjustable angle between the upper cover and the lower cover, wherein the relationship includes whether the adjustable angle satisfies a predefined angular criterion (e.g., whether the adjustable angle is zero (e.g., the lid is closed), is less than 5 degrees (e.g., the lid is mostly closed), is less than 20 degrees (e.g., the lid is partially closed), etc.).

Example 27 is the system of any one of examples 24 to 26, wherein the relationship includes a lid-closed mode, wherein the upper cover is flush (e.g., on all sides) with the lower cover when in the lid-closed mode.

Example 28 is the system of any one of examples 24 to 27, wherein the predefined trigger includes whether an amount of time has elapsed (e.g., after a last sanitization of the system).

Example 29 is the system of any one of examples 24 to 28, wherein the predefined trigger includes a change of a usage activity level of the system.

Example 30 is the system of any one of examples 24 to 29, wherein the predefined trigger includes reaching a predefined battery charge level of a battery of the system.

Example 31 is the system of any one of examples 24 to 30, wherein the keyboard includes an array of keys and/or a touchpad.

Example 32 is the system of any one of examples 24 to 31, the system further including a memory to store the predefined light intensity, the sanitization mode, and/or the predefined trigger.

Example 33 is the system of any one of examples 24 to 32, wherein the processor is configured to execute instructions configured to enable the sanitization mode for a predefined time period and disable the sanitization mode after the predefined time period.

Example 34 is the system of example 33, wherein the processor is configured to execute instructions configured to determine the predefined time period based on the predefined light intensity.

Example 35 is the system of any one of examples 24 to 34, wherein the predefined light intensity includes a predefined wavelength configuration of the light emitted by the display screen to sanitize the keyboard.

Example 36 is the system of example 35, wherein the predefined wavelength configuration includes blue wavelengths of light with an intensity that is higher than other wavelengths of the light emitted by the display screen.

Example 37 is the system of example 36, wherein the predefined wavelength configuration includes light wavelengths of between about 400 to about 500 nanometers.

Example 38 is the system of any one of examples 24 to 37, wherein the processor is configured to execute instructions configured to enable the sanitization mode based on a power mode of the system.

Example 39 is the system of example 38, wherein the power mode includes a battery-powered mode or an adapter-powered mode.

Example 40 is the system of any one of examples 24 to 39, wherein the processor is configured to execute instructions configured to disable the sanitization mode based on an end-sanitization event.

Example 41 is the system of example 40, wherein the end-sanitization event includes an elapsed time after enabling the sanitization mode.

Example 42 is the system of either one of examples 40 or 41, wherein the end-sanitization event includes a change of a usage activity level of the system.

Example 43 is the system of any one of examples 40 to 42, wherein the end-sanitization event includes reaching a predefined battery charge level of a battery of the system.

Example 44 is the system of any one of examples 40 to 43, wherein the end-sanitization event includes a change in a relationship between a location of the display screen and a location of the keyboard.

Example 45 is a method for self-sanitizing a device (e.g., a laptop), the method including determining a relationship between a location of a display of the device and a location of a keyboard surface of the device. The method also includes enabling a sanitization mode on the device based on the relationship, wherein when the sanitization mode is enabled, emitting light from the display toward the keyboard surface to sanitize the keyboard surface.

Example 46 is the method of example 45, wherein the relationship includes an angle of the display with respect to the keyboard surface.

Example 47 is the method of either one of examples 45 or 46, wherein the relationship includes a proximity of the display to the keyboard surface.

Example 48 is the method of any one of examples 45 to 47, wherein the keyboard surface includes a keyboard and/or a touchpad.

Example 49 is the method of any one of examples 45 to 48, the method further including storing (e.g., in a memory) the relationship.

Example 50 is the method of any one of examples 45 to 49, wherein the relationship includes a lid-closed mode, wherein the display is flush (e.g., on all sides) with the keyboard surface when in the lid-closed mode.

Example 51 is the method of any one of examples 45 to 50, wherein the device is a laptop and the display is connected to an A-cover of the laptop, wherein the display includes a B-cover of the laptop, wherein the keyboard surface includes a C-cover of the laptop.

Example 52 is the method of any one of examples 45 to 51, the method further including enabling the sanitization mode for a predefined time period and then disabling the sanitization mode after the predefined time period.

Example 53 is the method of example 52, the method further including determining the predefined time period based on an intensity level of the emitted light.

Example 54 is the method of any one of examples 45 to 53, the method further including causing the display to adjust a predefined wavelength configuration of the emitted light to sanitize the keyboard surface when the sanitization mode is enabled.

Example 55 is the method of example 54, wherein the predefined wavelength configuration includes a blue wavelength with an intensity that is higher than other wavelengths of the emitted light.

Example 56 is the method of example 55, wherein the blue wavelength is between about 400 and about 500 nanometers.

Example 57 is the method of any one of examples 45 to 56, the method further including enabling the sanitization mode based on a power mode of the device.

Example 58 is the method of example 57, wherein the power mode includes a battery-powered mode or an adapter-powered mode.

Example 59 is the method of any one of examples 45 to 58, the method further including enabling the sanitization mode based on a trigger event.

Example 60 is the method of example 59, wherein the trigger event includes an elapsed time after a previous self-sanitization of the device.

Example 61 is the method of either one of examples 59 or 60, wherein the trigger event includes a change of a usage activity level of the device.

Example 62 is the method of any one of examples 59 to 61, wherein the trigger event includes reaching a predefined battery charge level of a battery of the device.

Example 63 is the method of any one of examples 45 to 62, the method further including disabling the sanitization mode based on an end-sanitization event.

Example 64 is the method of example 63, wherein the end-sanitization event includes an elapsed time after enabling the sanitization mode.

Example 65 is the method of either one of examples 63 or 64, wherein the end-sanitization event includes a change of a usage activity level of the device.

Example 66 is the method of any one of examples 63 to 65, wherein the end-sanitization event includes reaching a predefined battery charge level of a battery of the device.

Example 67 is the method of any one of examples 63 to 66, wherein the end-sanitization event includes a change in the relationship between a location of the display and a location of the keyboard surface.

Example 68 is a method for self-sanitizing a device (e.g., a laptop), wherein the device includes an upper cover including a display screen and a lower cover including a keyboard, wherein the upper cover is connected by a hinge to the lower cover in a clamshell configuration. The method includes enabling a sanitization mode in the clamshell configuration based on a predefined trigger. The method also includes, emitting light with a predefined light intensity from the display screen toward the keyboard to sanitize the keyboard when the sanitization mode is enabled.

Example 69 is the method of example 68, wherein the predefined trigger includes a relationship between the upper cover and the lower cover.

Example 70 is the method of example 69, wherein the clamshell configuration provides an adjustable angle between the upper cover and the lower cover, wherein the relationship includes whether the adjustable angle satisfies a predefined angular criterion (e.g., whether the adjustable angle is zero (e.g., the lid is closed), is less than 5 degrees (e.g., the lid is mostly closed), is less than 20 degrees (e.g., the lid is partially closed), etc.).

Example 71 is the method of any one of examples 68 to 70, wherein the relationship includes a lid-closed mode where the upper cover is flush (e.g., on all sides) with the lower cover when in the lid-closed mode.

Example 72 is the method of any one of examples 68 to 71, wherein the predefined trigger includes whether an amount of time has elapsed (e.g., after a last sanitization of the device).

Example 73 is the method of any one of examples 68 to 72, wherein the predefined trigger includes a change of a usage activity level of the device.

Example 74 is the method of any one of examples 68 to 73, wherein the predefined trigger includes reaching a predefined battery charge level of a battery of the device.

Example 75 is the method of any one of examples 68 to 74, wherein the keyboard includes an array of keys and/or a touchpad.

Example 76 is the method of any one of examples 68 to 75, the method further including storing (e.g., in a memory) the predefined light intensity, the sanitization mode, and/or the predefined trigger.

Example 77 is the method of any one of examples 68 to 76, the method further including enabling the sanitization mode for a predefined time period and disabling the sanitization mode after the predefined time period.

Example 78 is the method of example 77, the method including determining the predefined time period based on the predefined light intensity.

Example 79 is the method of any one of examples 68 to 78, wherein the predefined light intensity includes a predefined wavelength configuration of the emitted light.

Example 80 is the method of example 79, wherein the predefined wavelength configuration includes blue wavelengths, wherein the predefined light intensity of the blue wavelengths have an intensity that is higher than other wavelengths of the emitted light.

Example 81 is the method of example 80, wherein the predefined wavelength configuration includes light wavelengths of between about 400 to about 500 nanometers.

Example 82 is the method of any one of examples 68 to 81, the method further including enabling the sanitization mode based on a power mode of the device.

Example 83 is the method of example 82, wherein the power mode includes a battery-powered mode or an adapter-powered mode.

Example 84 is the method of any one of examples 68 to 83, the method further including disabling the sanitization mode based on an end-sanitization event.

Example 85 is the method of example 84, wherein the end-sanitization event includes an elapsed time after enabling the sanitization mode.

Example 86 is the method of either one of examples 84 or 85, wherein the end-sanitization event includes a change of a usage activity level of the device.

Example 87 is the method of any one of examples 84 to 86, wherein the end-sanitization event includes reaching a predefined battery charge level of a battery of the device.

Example 88 is the method of any one of examples 84 to 87, wherein the end-sanitization event includes a change in a relationship between a location of the display screen and a location of the keyboard.

Example 89 is an apparatus (e.g., a self-sanitizing laptop), the apparatus includes a means for determining a relationship between a location of a display of the apparatus and a location of a keyboard surface of the apparatus. The apparatus also includes a means for enabling a sanitization mode on the apparatus based on the relationship and for causing the display to emit light toward the keyboard surface to sanitize the keyboard surface when the sanitization mode is enabled.

Example 90 is the apparatus of example 89, wherein the relationship includes an angle of the display with respect to the keyboard surface.

Example 91 is the apparatus of either one of examples 89 or 90, wherein the relationship includes a proximity of the display to the keyboard surface.

Example 92 is the apparatus of any one of examples 89 to 91, wherein the keyboard surface includes a keyboard and/or a touchpad.

Example 93 is the apparatus of any one of examples 89 to 92, the apparatus further including a means for storing (e.g., a memory) the relationship.

Example 94 is the apparatus of any one of examples 89 to 93, wherein the relationship includes a lid-closed mode, wherein the display is flush (e.g., on all sides) with the keyboard surface when in the lid-closed mode.

Example 95 is the apparatus of any one of examples 89 to 94, wherein the apparatus is a laptop and the display is connected to an A-cover of the laptop, wherein the display includes a B-cover of the laptop, wherein the keyboard surface includes a C-cover of the laptop.

Example 96 is the apparatus of any one of examples 89 to 95, the apparatus further including a means for enabling the sanitization mode for a predefined time period and then disabling the sanitization mode after the predefined time period.

Example 97 is the apparatus of example 96, the apparatus further including a means for determining the predefined time period based on an intensity level with which the display is caused to emit light toward the keyboard surface.

Example 98 is the apparatus of any one of examples 89 to 97, the apparatus further including a means for causing the display to adjust, when the sanitization mode is enabled, a predefined wavelength configuration of the light to sanitize the keyboard surface.

Example 99 is the apparatus of example 98, wherein the predefined wavelength configuration includes a blue wavelength of light with an intensity that is higher than other wavelengths of the light.

Example 100 is the apparatus of example 99, wherein the blue wavelength of light is between about 400 and about 500 nanometers.

Example 101 is the apparatus of any one of examples 89 to 100, the apparatus further including a means for enabling the sanitization mode based on a power mode of the apparatus.

Example 102 is the apparatus of example 101, wherein the power mode includes a battery-powered mode or an adapter-powered mode.

Example 103 is the apparatus of any one of examples 89 to 102, the apparatus further including a means for enabling the sanitization mode based on a trigger event.

Example 104 is the apparatus of example 103, wherein the trigger event includes an elapsed time after a previous self-sanitization of the apparatus.

Example 105 is the apparatus of either one of examples 103 or 104, wherein the trigger event includes a change of a usage activity level of the apparatus.

Example 106 is the apparatus of any one of examples 103 to 105, wherein the trigger event includes reaching a predefined battery charge level of a battery of the apparatus.

Example 107 is the apparatus of any one of examples 89 to 106, the apparatus further including a means for disabling the sanitization mode based on an end-sanitization event.

Example 108 is the apparatus of example 107, wherein the end-sanitization event includes an elapsed time after enabling the sanitization mode.

Example 109 is the apparatus of either one of examples 107 or 108, wherein the end-sanitization event includes a change of a usage activity level of the apparatus.

Example 110 is the apparatus of any one of examples 107 to 109, wherein the end-sanitization event includes reaching a predefined battery charge level of a battery of the apparatus.

Example 111 is the apparatus of any one of examples 107 to 110, wherein the end-sanitization event includes a change in the relationship between a location of the display and a location of the keyboard surface.

Example 112 is an apparatus (e.g., a self-sanitizing laptop), wherein the apparatus includes an upper cover including a display screen and a lower cover including a keyboard, wherein the upper cover is connected by a hinge to the lower cover in a clamshell configuration. The apparatus enables a sanitization mode in the clamshell configuration based on a predefined trigger and to cause the display screen to emit light with a predefined light intensity toward the keyboard to sanitize the keyboard when the sanitization mode is enabled.

Example 113 is the apparatus of example 112, wherein the predefined trigger includes a relationship between the upper cover and the lower cover.

Example 114 is the apparatus of example 113, wherein the clamshell configuration provides an adjustable angle between the upper cover and the lower cover, wherein the relationship includes whether the adjustable angle satisfies a predefined angular criterion (e.g., whether the adjustable angle is zero (e.g., the lid is closed), is less than 5 degrees (e.g., the lid is mostly closed), is less than 20 degrees (e.g., the lid is partially closed), etc.).

Example 115 is the apparatus of any one of examples 112 to 114, wherein the relationship includes a lid-closed mode where the upper cover is flush (e.g., on all sides) with the lower cover when in the lid-closed mode.

Example 116 is the apparatus of any one of examples 112 to 115, wherein the predefined trigger includes whether an amount of time has elapsed (e.g., after a last sanitization of the apparatus).

Example 117 is the apparatus of any one of examples 112 to 116, wherein the predefined trigger includes a change of a usage activity level of the apparatus.

Example 118 is the apparatus of any one of examples 112 to 117, wherein the predefined trigger includes reaching a predefined battery charge level of a battery of the apparatus.

Example 119 is the apparatus of any one of examples 112 to 118, wherein the keyboard includes an array of keys and/or a touchpad.

Example 120 is the apparatus of any one of examples 112 to 119, the apparatus further including a means for storing (e.g., in a memory) the predefined light intensity, the sanitization mode, and/or the predefined trigger.

Example 121 is the apparatus of any one of examples 112 to 120, the apparatus further including a means for enabling the sanitization mode for a predefined time period and disabling the sanitization mode after the predefined time period.

Example 122 is the apparatus of example 121, the apparatus including a means for determining the predefined time period based on the predefined light intensity.

Example 123 is the apparatus of any one of examples 112 to 122, wherein the predefined light intensity includes a predefined wavelength configuration of the light emitted by the display screen to sanitize the keyboard.

Example 124 is the apparatus of example 123, wherein the predefined wavelength configuration includes blue wavelengths of light with an intensity that is higher than other wavelengths of the light emitted by the display screen.

Example 125 is the apparatus of example 124, wherein the predefined wavelength configuration includes light wavelengths of between about 400 to about 500 nanometers.

Example 126 is the apparatus of any one of examples 112 to 125, the apparatus further including a means for enabling the sanitization mode based on a power mode of the apparatus.

Example 127 is the apparatus of example 126, wherein the power mode includes a battery-powered mode or an adapter-powered mode.

Example 128 is the apparatus of any one of examples 112 to 127, the apparatus further including a means for disabling the sanitization mode based on an end-sanitization event.

Example 129 is the apparatus of example 128, wherein the end-sanitization event includes an elapsed time after enabling the sanitization mode.

Example 130 is the apparatus of either one of examples 128 or 129, wherein the end-sanitization event includes a change of a usage activity level of the apparatus.

Example 131 is the apparatus of any one of examples 128 to 130, wherein the end-sanitization event includes reaching a predefined battery charge level of a battery of the apparatus.

Example 132 is the apparatus of any one of examples 128 to 131, wherein the end-sanitization event includes a change in a relationship between a location of the display screen and a location of the keyboard.

Example 133 is a non-transitory computer-readable medium for self-sanitizing a device (e.g., a laptop), the non-transitory computer-readable medium including instructions which, if executed, cause one or more processors to determine a relationship between a location of a display of the device and a location of a keyboard surface of the device. The instructions also cause the one or more processors to enable a sanitization mode on the device based on the relationship and to cause the display to emit light toward the keyboard surface to sanitize the keyboard surface when the sanitization mode is enabled.

Example 134 is the non-transitory computer-readable medium of example 133, wherein the relationship includes an angle of the display with respect to the keyboard surface.

Example 135 is the non-transitory computer-readable medium of either one of examples 133 or 134, wherein the relationship includes a proximity of the display to the keyboard surface.

Example 136 is the non-transitory computer-readable medium of any one of examples 133 to 135, wherein the keyboard surface includes a keyboard and/or a touchpad.

Example 137 is the non-transitory computer-readable medium of any one of examples 133 to 136, wherein the instructions also cause the one or more processors to store (e.g., in a memory) the relationship.

Example 138 is the non-transitory computer-readable medium of any one of examples 133 to 137, wherein the relationship includes a lid-closed mode, wherein the display is flush (e.g., on all sides) with the keyboard surface when in the lid-closed mode.

Example 139 is the non-transitory computer-readable medium of any one of examples 133 to 138, wherein the device is a laptop and the display is connected to an A-cover of the laptop, wherein the display includes a B-cover of the laptop, wherein the keyboard surface includes a C-cover of the laptop.

Example 140 is the non-transitory computer-readable medium of any one of examples 133 to 139, wherein the instructions also cause the one or more processors to enable the sanitization mode for a predefined time period and disable the sanitization mode after the predefined time period.

Example 141 is the non-transitory computer-readable medium of example 140, wherein the instructions also cause the one or more processors to determine the predefined time period based on an intensity level with which the display is caused to emit light toward the keyboard surface.

Example 142 is the non-transitory computer-readable medium of any one of examples 133 to 141, wherein the instructions also cause the display to adjust a predefined wavelength configuration of the light to sanitize the keyboard surface when the sanitization mode is enabled.

Example 143 is the non-transitory computer-readable medium of example 142, wherein the predefined wavelength configuration includes a blue wavelength of light with an intensity that is higher than other wavelengths of the light.

Example 144 is the non-transitory computer-readable medium of example 143, wherein the blue wavelength of light is between about 400 and about 500 nanometers.

Example 145 is the non-transitory computer-readable medium of any one of examples 133 to 144, wherein the instructions also cause the one or more processors to enable the sanitization mode based on a power mode of the device.

Example 146 is the non-transitory computer-readable medium of example 145, wherein the power mode includes a battery-powered mode or an adapter-powered mode.

Example 147 is the non-transitory computer-readable medium of any one of examples 133 to 146, wherein the instructions also cause the one or more processors to enable the sanitization mode based on a trigger event.

Example 148 is the non-transitory computer-readable medium of example 147, wherein the trigger event includes an elapsed time after a previous self-sanitization of the device.

Example 149 is the non-transitory computer-readable medium of either one of examples 147 or 148, wherein the trigger event includes a change of a usage activity level of the device.

Example 150 is the non-transitory computer-readable medium of any one of examples 147 to 149, wherein the trigger event includes reaching a predefined battery charge level of a battery of the device.

Example 151 is the non-transitory computer-readable medium of any one of examples 133 to 150, wherein the instructions also cause the one or more processors to disable the sanitization mode based on an end-sanitization event.

Example 152 is the non-transitory computer-readable medium of example 151, wherein the end-sanitization event includes an elapsed time after enabling the sanitization mode.

Example 153 is the non-transitory computer-readable medium of either one of examples 151 or 152, wherein the end-sanitization event includes a change of a usage activity level of the device.

Example 154 is the non-transitory computer-readable medium of any one of examples 151 to 153, wherein the end-sanitization event includes reaching a predefined battery charge level of a battery of the device.

Example 155 is the non-transitory computer-readable medium of any one of examples 151 to 154, wherein the end-sanitization event includes a change in the relationship between a location of the display and a location of the keyboard surface.

Example 156 is a non-transitory computer-readable medium that includes instructions which, if executed, cause one or more processors to enable a sanitization mode on a device (e.g., a laptop) based on a predefined trigger and to cause a display screen of the device to emit light with a predefined light intensity toward a keyboard to sanitize the keyboard when the sanitization mode is enabled.

Example 157 is the non-transitory computer-readable medium of example 156, wherein the predefined trigger includes a relationship between an upper cover and a lower cover of the device, wherein the upper cover is connected by a hinge to the lower cover in a clamshell configuration.

Example 158 is the non-transitory computer-readable medium of example 157, wherein the clamshell configuration provides an adjustable angle between the upper cover and the lower cover, wherein the relationship includes whether the adjustable angle satisfies a predefined angular criterion (e.g., whether the adjustable angle is zero (e.g., the lid is closed), is less than 5 degrees (e.g., the lid is mostly closed), is less than 20 degrees (e.g., the lid is partially closed), etc.).

Example 159 is the non-transitory computer-readable medium of any one of examples 156 to 158, wherein the relationship includes a lid-closed mode, wherein the upper cover is flush (e.g., on all sides) with the lower cover when in the lid-closed mode.

Example 160 is the non-transitory computer-readable medium of any one of examples 156 to 159, wherein the predefined trigger includes whether an amount of time has elapsed (e.g., after a last sanitization of the system).

Example 161 is the non-transitory computer-readable medium of any one of examples 156 to 160, wherein the predefined trigger includes a change of a usage activity level of the system.

Example 162 is the non-transitory computer-readable medium of any one of examples 156 to 161, wherein the predefined trigger includes reaching a predefined battery charge level of a battery of the device.

Example 163 is the non-transitory computer-readable medium of any one of examples 156 to 162, wherein the keyboard includes an array of keys and/or a touchpad.

Example 164 is the non-transitory computer-readable medium of any one of examples 156 to 163, wherein instructions also cause the one or more processors to store (e.g., in a memory) the predefined light intensity, the sanitization mode, and/or the predefined trigger.

Example 165 is the non-transitory computer-readable medium of any one of examples 156 to 164, wherein instructions also cause the one or more processors to enable the sanitization mode for a predefined time period and disable the sanitization mode after the predefined time period.

Example 166 is the non-transitory computer-readable medium of example 165, wherein the instructions also cause the one or more processors to determine the predefined time period based on the predefined light intensity.

Example 167 is the non-transitory computer-readable medium of any one of examples 156 to 166, wherein the predefined light intensity includes a predefined wavelength configuration of the light emitted by the display screen to sanitize the keyboard.

Example 168 is the non-transitory computer-readable medium of example 167, wherein the predefined wavelength configuration includes blue wavelengths of light with an intensity that is higher than other wavelengths of the light emitted by the display screen.

Example 169 is the non-transitory computer-readable medium of example 168, wherein the predefined wavelength configuration includes light wavelengths of between about 400 to about 500 nanometers.

Example 170 is the non-transitory computer-readable medium of any one of examples 156 to 169, wherein the instructions also cause the one or more processors to enable the sanitization mode based on a power mode of the device.

Example 171 is the non-transitory computer-readable medium of example 170, wherein the power mode includes a battery-powered mode or an adapter-powered mode.

Example 172 is the non-transitory computer-readable medium of any one of examples 156 to 171, wherein the instructions also cause the one or more processors disable the sanitization mode based on an end-sanitization event.

Example 173 is the non-transitory computer-readable medium of example 172, wherein the end-sanitization event includes an elapsed time after enabling the sanitization mode.

Example 174 is the non-transitory computer-readable medium of either one of examples 172 or 173, wherein the end-sanitization event includes a change of a usage activity level of the device.

Example 175 is the non-transitory computer-readable medium of any one of examples 172 to 174, wherein the end-sanitization event includes reaching a predefined battery charge level of a battery of the device.

Example 176 is the non-transitory computer-readable medium of any one of examples 172 to 175, wherein the end-sanitization event includes a change in a relationship between a location of the display screen and a location of the keyboard.

While the disclosure has been particularly shown and described with reference to specific aspects, it should be understood by those skilled in the art that various changes in form and detail may be made therein without departing from the spirit and scope of the disclosure as defined by the appended claims. The scope of the disclosure is thus indicated by the appended claims and all changes, which come within the meaning and range of equivalency of the claims, are therefore intended to be embraced.

The invention claimed is:

1. A device comprising a processor configured to execute computer instructions to:

determine a relationship between a location of a display of the device and a location of a keyboard surface of the device; and enable a sanitization mode on the device based on the relationship and to cause the display to emit visible light toward the keyboard surface to sanitize the keyboard surface when the sanitization mode is enabled, wherein the sanitation mode comprises a visible light output setting of a graphics controller of the display, wherein, based on the visible light output setting, the sanitation mode causes the display to output visible blue light from the display with a higher intensity as compared to visible green light output from the display and as compared to visible red light output from the display.

2. The device of claim 1, wherein the relationship comprises an angle of the display with respect to the keyboard surface or a proximity of the display to the keyboard surface.

3. The device of claim 1, wherein the keyboard surface comprises a keyboard or a touchpad.

4. The device of claim 1, the device further comprising a memory to store the relationship.

5. The device of claim 1, wherein the processor is configured to execute computer instructions to enable the sanitization mode for a predefined time period and disable the sanitization mode after the predefined time period.

6. The device of claim 5, wherein the processor is configured to execute instructions configured to determine the predefined time period based on an intensity level with which the display is caused to emit visible light toward the keyboard surface.

7. The device of claim 1, wherein when the sanitization mode is enabled, the computer instructions cause the display to adjust a predefined wavelength configuration of the visible light to sanitize the keyboard surface.

8. The device of claim 7, wherein the predefined wavelength configuration comprises a blue wavelength of visible blue light, a green wavelength of visible green light, and a red wavelength of visible red.

9. The device of claim 8, wherein the blue wavelength of light is between about 400 and about 500 nanometers.

10. The device of claim 1, wherein the processor is configured to execute computer instructions to enable the sanitization mode based on a trigger event, wherein the trigger event comprises an elapsed time after a previous self-sanitization of the device.

11. A system comprising:

an upper cover comprising a display screen;

a lower cover comprising a keyboard, wherein the upper cover is connected to the lower cover in a clamshell configuration by a hinge; and a processor configured to execute computer instructions to enable a sanitization mode in the clamshell configuration based on a predefined trigger and cause the display screen to emit visible light with a predefined light intensity toward the keyboard to sanitize the keyboard when the sanitization mode is enabled, wherein the sanitation mode comprises a visible light output setting of a graphics controller of the display screen for the predefined light intensity, wherein, based on the visible light output setting, the sanitation mode causes the display screen to output visible blue light from the display screen with a higher intensity as compared to visible green light output from the display screen and as compared to visible red light output from the display screen.

12. The system of claim 11, wherein the predefined trigger comprises a relationship between the upper cover and the lower cover.

13. The system of claim 12, wherein the clamshell configuration provides an adjustable angle between the upper cover and the lower cover, wherein the relationship comprises whether the adjustable angle satisfies a predefined angular criterion.

14. The system of claim 12, wherein the relationship comprises a lid-closed mode, wherein the upper cover is flush with the lower cover when in the lid-closed mode.

15. The system of claim 11, wherein the predefined trigger comprises a change of a usage activity level of the system.

16. The system of claim 11, wherein the predefined trigger comprises reaching a predefined battery charge level of a battery of the system.

17. The system of claim 11, wherein the processor is configured to execute instructions configured to disable the sanitization mode based on an end-sanitization event, wherein the end-sanitization event comprises an elapsed time after the sanitization mode is enabled, a change of a usage activity level of the system, a predefined battery charge level of a battery of the system, or a change in a relationship between a location of the display screen and a location of the keyboard.

18. A non-transitory computer-readable medium for self-sanitizing a device, the non-transitory computer-readable medium including instructions which, if executed, cause one or more processors to:

determine a relationship between a location of a display of the device and a location of a keyboard surface of the device; and enable a sanitization mode on the device based on the relationship and to cause the display to emit visible light toward the keyboard surface to sanitize the keyboard surface when the sanitization mode is enabled, wherein the sanitation mode comprises a visible light output setting of a graphics controller of the display, wherein, based on the visible light output setting, the sanitation mode causes the display to output visible blue light from the display with a higher intensity as compared to visible green light output from the display and as compared to visible red light output from the display.

19. The non-transitory computer-readable medium of claim 18, wherein the relationship comprises a lid-closed mode, wherein the display is flush with the keyboard surface when in the lid-closed mode.

20. The non-transitory computer-readable medium of claim 18, wherein the instructions also cause the one or more processors to enable the sanitization mode for a predefined time period and to disable the sanitization mode after the predefined time period.

\* \* \* \* \*